(12) United States Patent
Cigler

(10) Patent No.: US 8,617,425 B2
(45) Date of Patent: Dec. 31, 2013

(54) LIQUID COMPOSITION CONTAINING PHOSPHORIC OR THIOPHOSPHORIC TRIAMIDE DERIVATIVE AND USE THEREOF

(75) Inventor: Petr Cigler, Ceske Budejovice (CZ)

(73) Assignee: Agra Group, A.S., Strelske Hostice (CZ)

( * ) Notice: Subject to any disclaimer, the term of this patent is extended or adjusted under 35 U.S.C. 154(b) by 207 days.

(21) Appl. No.: 13/132,565

(22) PCT Filed: Dec. 21, 2009

(86) PCT No.: PCT/CZ2009/000161
§ 371 (c)(1), (2), (4) Date: Jun. 2, 2011

(87) PCT Pub. No.: WO2010/072184
PCT Pub. Date: Jul. 1, 2010

(65) Prior Publication Data
US 2011/0233474 A1    Sep. 29, 2011

(30) Foreign Application Priority Data
Dec. 23, 2008  (CZ) .............................. PV 2008-842

(51) Int. Cl.
C09K 15/32       (2006.01)
C05B 17/00       (2006.01)
C07F 9/22        (2006.01)

(52) U.S. Cl.
USPC ................. 252/400.22; 71/32; 71/54; 564/14

(58) Field of Classification Search
USPC ..................................................... 252/400.22
See application file for complete search history.

(56) References Cited

U.S. PATENT DOCUMENTS

| 4,530,714 | A | | 7/1985 | Kole et al. | |
|---|---|---|---|---|---|
| 5,364,438 | A | * | 11/1994 | Weston et al. | ..................... 71/29 |
| 2005/0233907 | A1 | * | 10/2005 | Nabors et al. | ................. 504/149 |
| 2007/0077428 | A1 | * | 4/2007 | Hamed et al. | ................. 428/393 |
| 2007/0184982 | A1 | * | 8/2007 | Long | ............................ 504/201 |

FOREIGN PATENT DOCUMENTS

| CZ | PV2006-422 | 6/2006 |
|---|---|---|
| WO | WO 98/27261 | 6/1998 |

* cited by examiner

*Primary Examiner* — Peter F Godenschwager
(74) *Attorney, Agent, or Firm* — Notaro, Michalos & Zaccaria P.C.

(57) ABSTRACT

The invention relates to a liquid composition containing phosphoric or thiophosphoric triamide derivatives and suitable solvents selected from the group comprising esters of hydroxyacids, heterocyclic alcohols and their derivatives, cyclic carbonic acid esters and dicarboxyacid esters, optionally the composition may also contain glycol ethers and auxiliary substances. The invention further includes the use of this liquid composition as urease inhibitor in urea-containing fertilizers, in fertilizers and wastes of animal origin or in sprays masking animal urine odors.

4 Claims, No Drawings

LIQUID COMPOSITION CONTAINING PHOSPHORIC OR THIOPHOSPHORIC TRIAMIDE DERIVATIVE AND USE THEREOF

FIELD OF ART

The invention relates to a liquid composition containing urease inhibitors based on phosphoric or thiophosphoric triamide derivatives, containing novel solvents.

BACKGROUND ART

Urea constitutes 46% of the worldwide consumption of nitrogen in agriculture and is the most widely used nitrogen fertilizer. However, after its application to soil, its partial hydrolysis to yield ammonia and carbon dioxide occurs. This process is catalysed by the enzyme urease, which is produced by some bacteria and fungi. The gaseous products formed by the hydrolysis reaction (ammonia and carbon dioxide) volatilize to the atmosphere and thus, substantial losses from the total amount of the nitrogen applied to the field occur.

The hydrolysis process can be considerably decelerated by urease inhibitors that are applied together with urea. Among the most effective urease inhibitors are the thiophosphoric triamide compounds disclosed in the U.S. Pat. No. 4,530,714, above all N-(n-butyl)thiophosphoric triamide (NBPT). The use of NBPT was experimentally verified and this compound is now industrially available for the use in agriculture (Watson, C. J. (2005) Proc. Internat. Fertiliser Soc. 454, 1-38).

The thiophosphoric triamides are used also for prevention of nitrogen loss from animal wastes (excrements, manure), which are caused by the enzymatic cleavage of urea present in the wastes to ammonia. According to WO 98/27261, urease inhibitors can be added to animal wastes also for the purpose of decreasing odour formation. Similarly, the urease inhibitors may be utilized in sprays masking animal urine odour, which are used for dissuading animals from undesired territorial behaviour including territory marking by urine.

Industrial grade N-(n-butyl)thiophosphoric triamide (NBPT) is a solid, waxy compound, which decomposes by the action of moisture and elevated temperature. With regard to its consistence, its direct application onto urea particles is very difficult. Technologically more advantageous is the use of the NBPT solutions in a suitable solvent, which should comply with some basic requirements: high solubility and stability of NBPT in the solvent, resistance of the NBPT solutions against the crystallization at a low temperature, low viscosity of the concentrated solutions of NBPT, low toxicity, volatility and flammability, minimum content of water in the commercially available form of the solvent, low cost.

In the U.S. Pat. No. 5,698,003, mixtures of N-(n-butyl) thiophosphoric triamide (NBPT) and aliphatic diols and triols or their esters are described, containing up to 50 wt. % of NBPT, preferably 20-30 wt. % of NBPT. These mixtures are suitable for the impregnation of granular urea, but they are liquid only at the temperatures above 15° C. Below this temperature, they solidify or crystallize. This undesired property renders the manipulation with the solutions and their application to granular urea in the course of its production, particularly during the cold periods of the year, when the temperature can fall deep below 0° C. U.S. Pat. No. 5,698,003 teaches that the addition of so-called "liquid amides" (e.g. 10 wt. % of N-methylpyrrolidone) to these solvents can shift the solidification temperature to 0° C. The liquid amides, however, are health-deleterious (N-methylpyrrolidone is often classified among carcinogenic and teratogenic compounds) and the solidifying temperature achieved is still not sufficient for the manipulation at low temperatures or at freezing.

Another issue is the technical quality and hygroscopicity of the commercially available diols and triols. They often contain few tenths of percent of water and this amount can further increase during storage due to the hygroscopicity of the solvents. During a longer storage period, the presence of water causes the decomposition of N-(n-butyl)thiophosphoric triamide (NBPT) into non-effective substances and is the main cause of the NBPT degradation during a long-term storage. The instability of NBPT towards hydrolysis is well known, e.g. because of it, NBPT is poorly utilizable on moist soils.

Czech patent application PV 2006-422 teaches a solvent system for the preparation of N-alkyl thiophosphoric triamide solutions containing glykolethers, and optionally further auxiliary substances, such as N-methylpyrrolidone or polyvinylpyrrolidone. The glycolethers show excellent solvent properties, but they belong among synthetic solvents. For both ecological and legislative reasons, it is at present more advantageous to use so-called "green" solvents, that decompose to natural substances in the ecosystem.

The above mentioned disadvantages can be solved by liquid compositions of N-alkyl phosphoric or thiophosphoric triamides with a new group of solvents according to the present invention.

DISCLOSURE OF THE INVENTION

Object of the present invention is a liquid composition containing
at least one phosphoric or thiophosphoric triamide derivative of general formula (VIII),

$$R^6R^7N(NH_2)_2P=Y \quad (VIII)$$

wherein Y is oxygen or sulphur atom and $R^6$ and $R^7$ are independently selected from the group comprising hydrogen, $C_1$-$C_{10}$ alkyl, $C_3$-$C_{10}$ cycloalkyl, $C_6$-$C_{10}$ aryl and di(hydrocarbyl)aminocarbonyl, in which the hydrocarbyls can be the same or different and are selected from the group comprising $C_1$-$C_{10}$ alkyl, $C_3$-$C_{10}$ cycloalkyl, $C_6$-$C_{10}$ aryl, or $R^6$ and $R^7$ together with the nitrogen atom, to which they are bound, may form a heterocyclic ring containing 1 to 5 carbon atoms and optionally further one or two heteroatoms selected from the group comprising nitrogen, sulphur and oxygen, whereas the alkyl, cycloalkyl, aryl and heterocyclic moieties may optionally be substituted with one to five groups selected from the group comprising halogen, nitro, amino, hydroxy, methoxy and ethoxy substituents. The alkyl groups may include, e.g., methyl, ethyl, propyl, isopropyl, butyl, isobutyl, sec-butyl, tert-butyl, pentyl, isopentyl, neopentyl, tert-pentyl, hexyl, 2-methylpentyl, heptyl, octyl, 2-ethylhexyl, isoctyl, nonyl, isononyl, decyl, isodecyl. Cycloalkyl groups may include, e.g., cyclopropyl, cyclobutyl, cyclopentyl, cyclohexyl and cyclooktyl. Aryl groups may include, e.g., phenyl or naphthyl. $R^6R^7N$ heterocyclic rings may be, e.g., piperazinyl, morpholinyl, pyrrolyl, pyrazolyl, triazolyl, oxazolyl, thiazolyl or imidazolyl,
and one or more compounds selected from the group comprising
a) esters of hydroxyacids of general formula I,

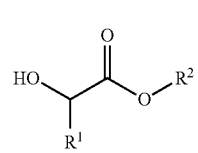

(I)

wherein R¹ is hydrogen or methyl, R² is $C_1$ to $C_6$ primary alkyl, $C_3$ to $C_6$ secondary alkyl or $C_4$ to $C_6$ tertiary alkyl;

b) heterocyklic alcohols and derivatives thereof of general formula II,

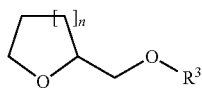
(II)

wherein n=1 or 2, R³ is hydrogen, $C_1$ to $C_4$ primary alkyl, $C_3$ to $C_4$ secondary alkyl or $C_1$ to $C_4$ acyl
and heterocyclic alcohols of formulas III, IV a V;

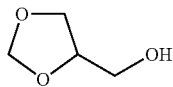
(III)

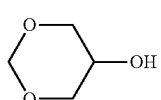
(IV)

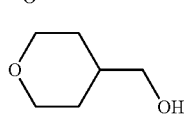
(V)

c) cyclic esters of carbonic acid of general formula VI,

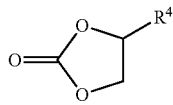
(VI)

wherein R⁴ is hydrogen, $C_1$ to $C_4$ alkyl or $C_1$ to $C_2$ hydroxyalkyl;
and
d) esters of dicarboxyacids of general formula VII

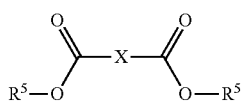
(VII)

wherein X is $C_1$ to $C_6$ alkylene or $C_2$ to $C_6$ alkenylene and R⁵ is $C_1$ to $C_6$ primary alkyl, $C_3$ to $C_6$ secondary alkyl or $C_4$ to $C_6$ tertiary alkyl,
whereas the composition may optionally further contain auxiliary substances improving the stability and application properties of the solutions.

Herein, the substituent names have the following meanings: aryl is a group containing at least one aromatic cycle, halogen is selected from the group comprising fluorine, chlorine, bromine, iodine, nitro denotes the group —$NO_2$, amino denotes the group —$NH_2$, hydroxy denotes the group —OH, methoxy denotes the group —$OCH_3$ and ethoxy denotes the group —$OCH_2CH_3$.

Hydroxyacid esters of the general formula I may be in the form of optically active isomers, when R¹ is methyl. In a preferred embodiment, S-isomers of hydroxyacid esters are used. Preferred compounds of the general formula I are methyl lactate, ethyl lactate, methyl glycolate, and ethyl glycolate.

The compounds of formulas II, III and VI may be used in the form of any optically active isomer or mixture of isomers.

Esters of unsaturated dicarboxylic acids of formula VII may form E- and Z-isomers. In a preferred embodiment, Z-isomers of the esters of unsaturated dicarboxylic acids are used. Preferred compounds of general formula VII are methyl malonate, ethyl malonate, methyl maleate and ethyl maleate.

In a preferred embodiment, the liquid composition comprises:
at least one phosphoric or thiophosphoric triamide derivative of general formula (VIII),

$R^6R^7N(NH_2)_2P=Y$ (VIII)

wherein Y is oxygen or sulfur atom, and R⁶ and R⁷ are independently selected from the group comprising hydrogen, $C_1$-$C_{10}$ alkyl, $C_3$-$C_{10}$ cycloalkyl, $C_6$-$C_{10}$ aryl and di(hydrocarbyl)aminocarbonyl, in which the hydrocarbyls can be the same or different and are selected from the group comprising $C_1$-$C_{10}$ alkyl, $C_3$-$C_{10}$ cycloalkyl, $C_6$-$C_{10}$ aryl, or R⁶ and R⁷ together with the nitrogen atom, to which they are bound, may form a heterocyclic ring containing 1 to 5 carbon atoms and optionally further one or two heteroatoms selected from the group comprising nitrogen, sulfur and oxygen, whereas the alkyl, cycloalkyl and aryl substituents may optionally be substituted by one to five groups selected from the group comprising halogen, nitro, amino, hydroxy, methoxy and ethoxy substituents;

at least one compound of general formula I selected from the group comprising methyl lactate, ethyl lactate, methyl glycolate, ethyl glycolate, preferably, the compound of general formula I is ethyl lactate, and optionally one or more compounds selected from the group comprising b) heterocyclic alcohols and derivatives thereof of general formula II,

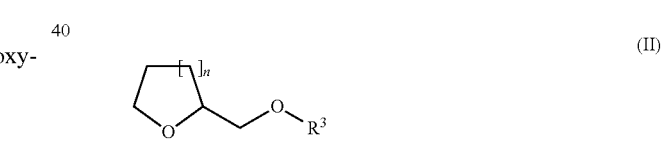
(II)

wherein n=1 or 2, R³ is hydrogen, $C_1$ to $C_4$ primary alkyl $C_3$ to $C_4$ secondary alkyl or $C_1$ to $C_4$ acyl,
and heterocyclic alcohols of formulas III, IV and V,

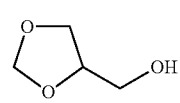
(III)

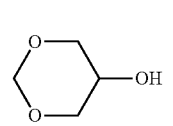
(IV)

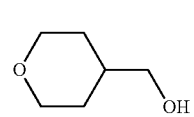
(V)

c) cyclic esters of carbonic acid of general formula VI,

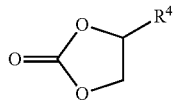

wherein $R^4$ is hydrogen, $C_1$ to $C_4$ alkyl or $C_1$ to $C_2$ hydroxyalkyl
and
d) esters of dicarboxyacids of general formula VII

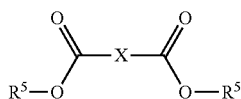

wherein X is $C_1$ to $C_6$ alkylene or $C_2$ to $C_6$ alkenylene and $R^5$ is $C_1$ to $C_6$ primary alkyl, $C_3$ to $C_6$ secondary alkyl or $C_4$ to $C_6$ tertiary alkyl;
whereas the composition may optionally contain further auxiliary substances enhancing the stability and application properties of the solutions.

The auxiliary substances enhancing the stability and application properties of solutions may be, e.g., crystallization inhibitors, surface active agents, or colorants. In a preferred embodiment, the crystallization inhibitors may be polyvinylpyrrolidone or N-methylpyrrolidone. Preferably, the crystallization inhibitor used is polyvinylpyrrolidone in the concentration range of from 0.01 to 5% w/w. This substance is non-toxic and is used in similar concentrations in, e.g., medicine as an additive to eye drops. For indication of homogeneity of the coverage of a solid urea-containing fertilizer (e.g., granulated urea) surface by the solution of the phosphoric or thiophosphoric triamide derivative, colorants commonly used in agriculture or food industry may be added to the solution. In order to achieve a sufficient coverage of a solid urea-containing fertilizer (e.g., granulated urea) surface by the solution of the phosphoric or thiophosphoric triamide derivative, surface active agents such as those commonly used in agriculture for this purpose may be added to the solution.

The liquid composition according to the present invention can further contain at least one glycol ether of the general formula (IX)

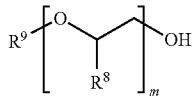

wherein $R^8$ is hydrogen or methyl, $R^9$ is a substituent selected from the group comprising $C_1$-$C_6$ primary alkyl, $C_3$-$C_6$ isoalkyl, $C_4$-$C_6$ tertiary alkyl, m=2-4.

In a preferred embodiment, the composition contains at least one phosphoric or thiophosphoric triamide derivative of general formula (VIIIa), $$R^{6a}NH(NH_2)_2P=Y \quad \text{(VIIIa)}$$

wherein Y is oxygen or sulfur atom and $R^{6a}$ is selected from the group comprising linear or branched alkyl chains having 1 to 8 carbon atoms, cycloalkyl chains having 3 to 8 carbon atoms and aryl groups containing 6 to 10 carbon atoms, whereas these alkyl, cycloalkyl and aryl substituents may optionally be substituted by one to five groups selected from the group comprising halogen, nitro, amino, hydroxy, methoxy and ethoxy substituents. Preferably, the phosphoric or thiophosphoric triamide derivative of general formula VIIIa is selected from the group comprising N-(n-butyl) thiophosphoric acid triamide, N-cyclohexyl thiophosphoric acid triamide and N-(2-nitrophenyl) phosphoric acid triamide.

Preferably, the composition of the present invention contains 5 to 50% w/w of the phosphoric or thiophosphoric triamide derivative of general formula VIII, preferably of N-(n-butyl) thiophosphoric triamide, N-cyclohexyl thiophosphoric triamide or N-(2-nitrophenyl) phosphoric triamide.

More preferably, the composition of the present invention contains 10 to 40% w/w of the phosphoric or thiophosphoric triamide derivative of general formula VIII, preferably of N-(n-butyl) thiophosphoric triamide, N-cyclohexyl thiophosphoric triamide or N-(2-nitrophenyl) phosphoric triamide.

Most preferably, the composition of the present invention contains 20 to 30% w/w of the phosphoric or thiophosphoric triamide derivative of general formula VIII, preferably of N-(n-butyl) thiophosphoric triamide, N-cyclohexyl thiophosphoric triamide or N-(2-nitrophenyl) phosphoric triamide.

Another object of the present invention is the use of the composition containing the phosphoric or thiophosphoric triamide derivative as urease inhibitor in urea-containing fertilizers. The urea-containing fertilizers may be solid, then the composition according to the present invention can be added to the mixture during the manufacture of these fertilizers, or the particles of the fertilizer, e.g., granules, can be impregnated by the composition of the present invention. In another embodiment of the present invention, the urea-containing fertilizers may be liquid, and then the composition of the present invention can be mixed with the liquid fertilizer. The composition can also be added to fertilizers and wastes of animal origin (excrements, manure) in order to decrease nitrogen loss and odour formation. The composition can also be added into sprays masking the animal urine odours.

The solvents according to the present invention have properties that are advantageous for their use in agriculture: a high concentration of phosphoric or thiophosphoric triamide derivatives, such as N-(n-butyl) thiophosphoric acid triamide (NBPT), in the solution can be achieved and the derivatives (such as NBPT) are stabilized in these solutions.

The solvents of the present invention are degradable to naturally occurring substances (e.g., lactic acid and ethanol for ethyl lactate, carbon dioxide and diols for carbon acid cyclic esters) and thus belong among "green" solvents. The importance of these solvents is gradually increasing, because their use does not add toxic residues into the environment. The solvents of the invention further show a high resistance against solidifying and crystallization at low temperatures, are water-miscible, they are not toxic and have a low volatility and flammability. Due to their solvent and chemical properties, the solvent systems of the invention are suitable for impregnation of granular urea and for addition into liquid fertilizers containing water as the solvent. Another advantage is their low cost.

The invention is further illustrated by way of examples, which should not be construed as further limiting.

EXAMPLES

Example 1

Preparation of Solution of N-(n-butyl)thiophosphoric triamide in (S)-ethyl lactate 2.0 kg of N-(n-butyl)thiophosphoric triamide was slowly added to 8.0 kg of (S)-ethyl lactate under stirring. A clear solution was formed.

Example 2

Preparation of Solution of N-(n-butyl)thiophosphoric triamide in the Mixture of (S)-ethyl lactate and dimethyl malonate 2.0 kg of N-(n-butyl)thiophosphoric triamide was slowly added to the mixture of 3.0 kg of (S)-ethyl lactate and 5.0 kg of dimethyl malonate under stirring. A clear solution was formed.

Example 3

The solutions of N-(n-butyl) thiophosphoric triamide (NBPT) in the solvent systems of the present invention have the capability to remain liquid at very low temperatures. This capability is due to the chemical nature of the solvents. In this example, stability against crystallization and flowability of the compositions of the invention is described.

The concentration of technical-grade NBPT in the solutions was 20 wt. %. For testing, the temperature −5° C. was selected. After 1 month of storage the presence of crystals in the solutions (yes-no) and the flowability of the solutions were assessed. The composition of the liquid compositions and the results are summarized in Table 1.

Abbreviations Used:
(S)-ethyl lactate EL
propylene carbonate PC
tetrahydrofurfuryl alcohol THFA
polyvinylpyrrolidone PVP
N-methylpyrrolidone NMP
glycerol formal GF
propylene glycol PG All prepared solutions showed an excellent flowability. The solvent systems have proven very technologically suitable for the preparation of NBPT solutions, because highly concentrated compositions containing 20 wt. % of NBPT do not crystallize at a low temperature and maintain an excellent flowability also after cooling. Binary (A, B, E, F and G) and ternary (C) solvent systems have similar properties. The addition of crystallization inhibitor polyvinylpyrrolidone (composition D) does not adversely affect the flowability of the solution. All solvent systems are water-miscible.

For comparison with the prior art, a mixture containing propylene glycol (PG) with 10 wt. % N-methylpyrrolidone (NMP) described in the U.S. Pat. No. 5,698,003 was used. This mixture crystallized under said conditions.

Example 4

A high stability of N-(n-butyl)thiophosphoric triamide (NBPT) in the solvent system is the key feature for long-term storage of its solutions. The presence of water causes the decomposition of NBPT into non-effective substances during a longer storage and is the main cause of the NBPT degradation during a long-term storage.

The solvent systems of the present invention show a stabilizing effect towards NBPT. All solvents used in this example are commercially available in a very good quality, having the water content lower than 0.1 wt. %. Nevertheless, to confirm the stabilization effect of the solvents, the water content was artificially increased to 1 wt. %. The thus adjusted solvent systems simulate the effect of the moisture on NBPT (higher contents of the moisture than 1 wt. % are uncommon).

In order to verify the long-term stability of NBPT, the following solvents containing less than 0.1 wt. % of water were selected, which are characterized in Table 2.

TABLE 2

Composition of solvents

| Designation | Composition of the solvent |
|---|---|
| NR1 | (S)-ethyl lactate |
| NR3 | propylene carbonate |
| NR5 | mixture containing 33 wt. % of ethyl lactate and 67 wt. % of propylene carbonate |

These solvents were further adjusted to 1 wt. % water content, whereby the solvents characterized in Table 3 were obtained.

TABLE 1

Effect of the composition of the solvent systems on the crystallization of NBPT from its solutions at the temperature of −5° C.

| Composition | Crystallization at −5° C. | Composition components (wt. %) | | | | | | |
|---|---|---|---|---|---|---|---|---|
| | | NBPT | EL | PC | THFA | PVP | GF | NMP | PG |
| A | no | 20 | 40 | | 40 | | | | |
| B | no | 20 | 10 | | 70 | | | | |
| C | no | 20 | 40 | 10 | 30 | | | | |
| D | no | 20 | 39 | | 40 | 1 | | | |
| E | no | 20 | 50 | | | | 30 | | |
| F | no | 20 | 40 | | | | 40 | | |
| G | no | 20 | 30 | | | | 50 | | |
| H | yes | 20 | | | | | | 10 | 70 |

TABLE 3

Composition of solvents containing 1 wt. % water.

| Designation | Composition of the solvent |
|---|---|
| NR2 | (S)-ethyl lactate containing 1 wt. % water |
| NR4 | propylene carbonate containing 1 wt. %w ater |
| NR6 | mixture containing 33 wt. % of ethyl lactate and 67 wt. % of propylene carbonate, further containing 1 wt. % water |

The solutions of NBPT in these solvents having the concentration ca 20 wt. % (weighed portion) were stored at room temperature at daylight in glass, well-sealed vials.

The determination of the content of NBPT was carried out by reverse-phase HPLC with UV detection in the mobile phase containing 25 vol. % acetonitrile and 75 vol. % 0.005M ammonium acetate. The chromatogram was evaluated at the wavelength of 193 nm. The mobile phase flow was 1 ml/min, the column temperature was 40° C. The injected volume was 5 μl. The evaluation was carried out by the method of external standard with the calibration using a calibration line. The results are summarized in Tab. 4.

TABLE 4

Summary of the results (in wt. %) of the determination of NBPT content in time from the preparation of the composition.

| | NBPT content (wt. %) | | | | | | |
|---|---|---|---|---|---|---|---|
| | 0 days | | 14 days | | 39 days | | 3 months |
| Designation | | RSD (%) | | RSD (%) | | RSD (%) | | RSD (%) |
| NR1 | 19.62 | 1.74 | 19.66 | 1.40 | 19.51 | 0.84 | 19.46 | 1.35 |
| NR2 | 20.08 | 1.63 | 19.90 | 1.39 | 19.45 | 2.16 | 19.59 | 0.84 |
| NR3 | 19.62 | 0.90 | 19.46 | 2.05 | 19.45 | 1.53 | 19.61 | 1.00 |
| NR4 | 19.82 | 1.18 | 19.50 | 1.20 | 19.41 | 1.33 | 19.51 | 1.10 |
| NR5 | 19.83 | 1.22 | 19.78 | 0.87 | 19.54 | 1.16 | 19.51 | 0.86 |
| NR6 | 20.00 | 1.91 | 19.67 | 0.67 | 19.32 | 0.97 | 19.30 | 0.32 |

RSD is the relative deviation in rel. %, calculated from three repeats of sampling and two repeats of analysis of each sample.

The results show that the solvent systems of the present invention have a stabilizing effect towards NBPT, even at the water content of 1 wt. %. After twelve weeks of storage, no significant decrease of the content of the active component NBPT occurred in any sample (the method used can determine the change of approx. at least 1 wt. %).

Example 5

Preparation of Granulated Urea Containing N-(n-butyl)thiophosphoric triamide 1 ton of granulated urea was impregnated in an impregnation machine by 3 kg of the composition of example 1 containing 20 wt. % NBPT, into which food colorants were added (Brilliant Blue FCF, 0.033% and Ponceau 4R, 0.033%) in order to assess the homogeneity of the coverage of the granule surface. It was observed that the composition was homogeneously distributed on the granule surface.

INDUSTRIAL APPLICABILITY

The solutions of N-alkyl phosphoric or thiophosphoric triamides in the solvent systems of the present invention can be long-term stored, used for the impregnation of solid urea-containing fertilizers, such as granular urea, added into the mixture for the manufacture of solid urea-containing fertilizers or added into liquid urea-containing fertilizers. They can also be used as a suitable urease inhibitor formulation for addition into animal wastes or sprays masking urine odour.

The invention claimed is:

1. A liquid composition, characterized in that it comprises:
   5 to 50% wt/wt of at least one phosphoric or thiophosphoric triamide derivative of general formula (VIII), $$R^6R^7N(NH_2)_2P=Y \quad (VIII)$$

wherein Y is oxygen or sulfur atom, and $R^6$ and $R^7$ are independently selected from the group consisting of hydrogen, $C_1$-$C_{10}$ alkyl, $C_3$-$C_{10}$ cycloalkyl, $C_6$-$C_{10}$ aryl and di(hydrocarbyl)aminocarbonyl, in which the hydrocarbyls can be the same or different and are selected from the group consisting of $C_1$-$C_{10}$ alkyl, $C_3$-$C_{10}$ cycloalkyl, $C_6$-$C_{10}$ aryl, and $R^6$ and $R^7$ together with the nitrogen atom, to which they are bound, may form a heterocyclic ring containing 1 to 5 carbon atoms and optionally further one or two heteroatoms selected from the group consisting of nitrogen, sulfur and oxygen, whereas the alkyl, cycloalkyl and aryl substituents may optionally be substituted by one to five groups selected from the group consisting of halogen, amino, hydroxy, methoxy and ethoxy substituents;

at least one compound selected from the group consisting of methyl lactate, ethyl lactate, methyl glycolate, ethyl glycolate, and optionally one or more compounds selected from the group consisting of b) heterocyclic alcohols and derivatives thereof of general formula II,

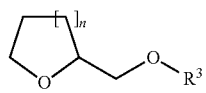
(II)

wherein n=1 or 2, $R^3$ is hydrogen, $C_1$ to $C_4$ primary alkyl $C_3$ to $C_4$ secondary alkyl or $C_1$ to $C_4$ acyl,
   and heterocyclic alcohols of formulas III, IV and V,

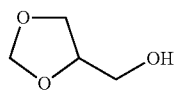
(III)

-continued

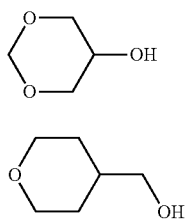

(IV)

(V)

c) cyclic esters of carbonic acid of general formula VI,

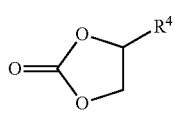
(VI)

wherein $R^4$ is hydrogen, $C_1$ to $C_4$ alkyl or $C_1$ to $C_2$ hydroxyalkyl and d) esters of dicarboxyacids of general formula VII

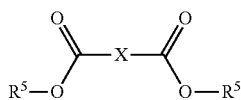
(VII)

wherein X is $C_1$ to $C_6$ alkylene or $C_2$ to $C_6$ alkenylene and $R^5$ is $C_1$ to $C_6$ primary alkyl, $C_3$ to $C_6$ secondary alkyl or $C_4$ to $C_6$ tertiary alkyl whereas the composition may optionally contain further auxiliary substances enhancing the stability and application properties of the solutions.

2. A liquid composition, characterized in that it contains:

at least one phosphoric or thiophosphoric triamide derivative of general formula (VIII),

$R^6R^7N(NH_2NH_2)_2P=Y$ (VIII)

wherein Y is oxygen or sulphur atom and $R^6$ and $R^7$ are independently selected from the group consisting of hydrogen $C_1$-$C_{10}$ alkyl, $C_3$-$C_{10}$ cycloalkyl, $C_6$-$C_{10}$ aryl and di(hydrocarbyl)aminocarbonyl, in which the hydrocarbyls can be the same or different and are selected from the group consisting of $C_1$-$C_{10}$ alkyl, $C_3$-$C_{10}$ cycloalkyl, $C_6$-$C_{10}$ aryl, and $R^6$ and $R^7$ together with the nitrogen atom, to which they are bound, may form a heterocyclic ring containing 1 to 5 carbon atoms and optionally further one or two heteroatoms selected from the group consisting of nitrogen, sulphur and oxygen, whereas the alkyl, cycloalkyl, aryl and heterocyclic moieties may optionally be substituted with one to five groups selected from the group consisting of halogen, amino, hydroxy, methoxy and ethoxy substituents;

and one or more compounds selected from the group consisting of a) esters of hydroxyacids of general formula I,

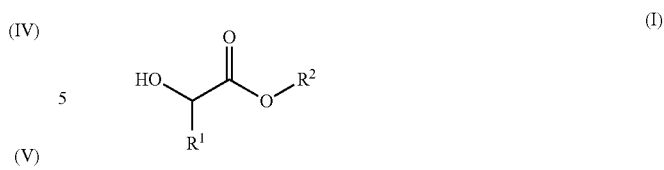
(I)

wherein $R^1$ is hydrogen or methyl, $R^2$ is $C_1$ to $C_6$ primary alkyl, $C_3$ to $C_6$ secondary alkyl or $C_4$ to $C_6$ tertiary alkyl;

b) heterocyclic alcohols and derivatives thereof of general formula II,

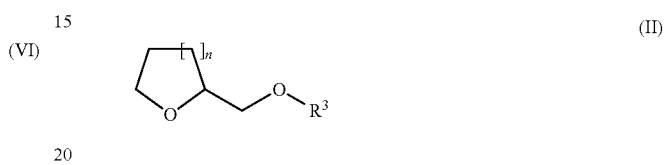
(II)

wherein n=1 or 2, $R^3$ is hydrogen, $C_1$ to $C_4$ primary alkyl, $C_3$ to $C_4$ secondary alkyl or $C_1$ to $C_4$ acyl;

and heterocyclic alcohols of formulas III, IV a V;

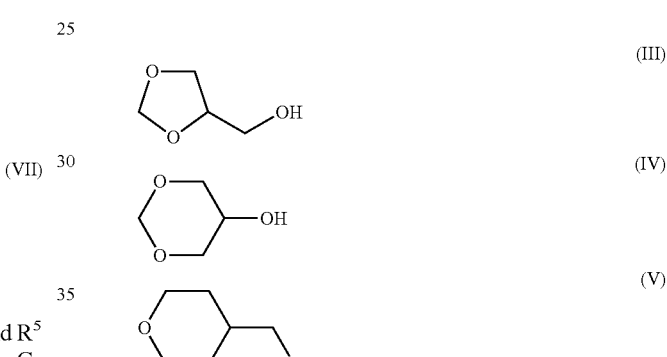
(III)

(IV)

(V)

c) cyclic esters of carbonic acid of general formula VI, (VI)

wherein $R^4$ is hydrogen, or $C_1$ to $C_2$ hydroxyalkyl; and d) esters of dicarboxyacids of general formula VII

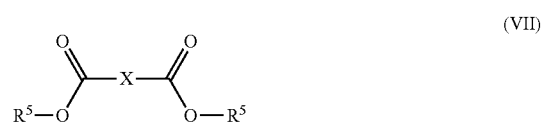
(VII)

wherein X is $C_1$ to $C_6$ alkylene or $C_2$ to $C_6$ alkenylene and $R^5$ is $C_1$ to $C_6$ primary alkyl or $C_4$ to $C_6$ tertiary alkyl, whereas the composition may optionally further contain auxiliary substances improving the stability and application properties of the solutions, characterized in that it contains 5 to 50% wt/wt of the phosphoric or thiophosphoric triamide derivative of general formula VIII.

3. A liquid composition, characterized in that it contains:

at least one phosphoric or thiophosphoric triamide derivative of general formula (VIII), $$R^6R^7N(NH_2)_2P=Y \quad \text{(VIII)}$$

wherein Y is oxygen or sulphur atom and $R^6$ and $R^7$ are independently selected from the group consisting of hydrogen, $C_1$-$C_{10}$ alkyl, $C_3$-$C_{10}$ cycloalkyl, $C_6$-$C_{10}$ aryl and di(hydrocarbyl)aminocarbonyl, in which the hydrocarbyls can be the same or different and are selected from the group consisting of $C_1$-$C_{10}$ alkyl, $C_3$-$C_{10}$ cycloalkyl, $C_6$-$C_{10}$ aryl, and $R^6$ and $R^7$ together with the nitrogen atom, to which they are bound, may form a heterocyclic ring containing 1 to 5 carbon atoms and optionally further one or two heteroatoms selected from the group consisting of nitrogen, sulphur and oxygen, whereas the alkyl, cycloalkyl, aryl and heterocyclic moieties may optionally be substituted with one to five groups selected from the group consisting of halogen, amino, hydroxy, methoxy and ethoxy substituents;

and one or more compounds selected from the group consisting of a) esters of hydroxyacids of general formula I,

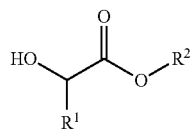

(I)

wherein $R^1$ is hydrogen or methyl, $R^2$ is $C_1$ to $C_6$ primary alkyl, $C_3$ to $C_6$ secondary alkyl or $C_4$ to $C_6$ tertiary alky;

b) heterocyclic alcohols and derivatives thereof of general formula II,

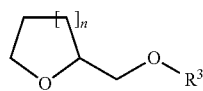

(II)

wherein n=1 or 2, $R^3$ is hydrogen, $C_1$ to $C_4$ primary alkyl, $C_3$ to $C_4$ secondary alkyl or $C_1$ to $C_4$ acyl;

and heterocyclic alcohols of formulas III, IV a V;

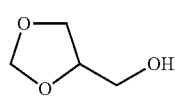

(III)

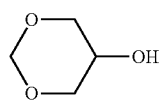

(IV)

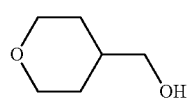

(V)

c) cyclic esters of carbonic acid of general formula VI,

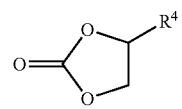

(VI)

wherein $R^4$ is hydrogen, or $C_1$ to $C_2$ hydroxyalkyl;
and d) esters of dicarboxyacids of general formula VII

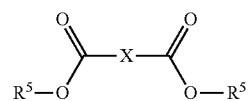

(VII)

wherein X is $C_1$ to $C_6$ alkylene or $C_2$ to $C_6$ alkenylene and $R^5$ is $C_1$ to $C_6$ primary alkyl, or $C_4$ to $C_6$ tertiary alkyl, whereas the composition may optionally further contain auxiliary substances improving the stability and application properties of the solutions, characterized in that it contains 10 to 40% wt/wt of the phosphoric or thiophosphoric triamide derivative of general formula VIII.

4. A liquid composition, characterized in that it contains:

at least one phosphoric or thiophosphoric triamide derivative of general formula (VIII), $$R^6R^7N(NH_2)_2P=Y \quad \text{(VIII)}$$

wherein Y is oxygen or sulphur atom and $R^6$ and $R^7$ are independently selected from the group consisting of hydrogen, $C_1$-$C_{10}$ alkyl, $C_3$-$C_{10}$ cycloalkyl, $C_6$-$C_{10}$ aryl and di(hydrocarbyl)aminocarbonyl, in which the hydrocarbyls can be the same or different and are selected from the group consisting of $C_1$-$C_{10}$ alkyl, $C_3$-$C_{10}$ cycloalkyl, $C_6$-$C_{10}$ aryl, and $R^6$ and $R^7$ together with the nitrogen atom, to which they are bound, may form a heterocyclic ring containing 1 to 5 carbon atoms and optionally further one or two heteroatoms selected from the group consisting of nitrogen, sulphur and oxygen, whereas the alkyl, cycloalkyl, aryl and heterocyclic moieties may optionally be substituted with one to five groups selected from the group consisting of halogen, amino, hydroxy, methoxy and ethoxy substituents;

and one or more compounds selected from the group consisting of a) esters of hydroxyacids of general formula I,

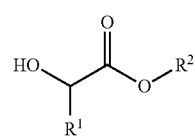

(I)

wherein $R^1$ is hydrogen or methyl, $R^2$ is $C_1$ to $C_6$ primary alkyl, $C_3$ to $C_6$ secondary alkyl or $C_4$ to $C_6$ tertiary alkyl;

b) heterocyclic alcohols and derivatives thereof of general formula II,

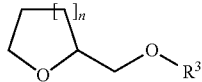 (II)

wherein n=1 or 2, $R^3$ is hydrogen, $C_1$ to $C_4$ primary alkyl, $C_3$ to $C_4$ secondary alkyl or $C_1$ to $C_4$ acyl;
and heterocyclic alcohols of formulas III, IV a V;

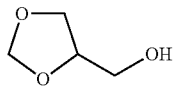 (III)

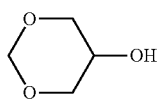 (IV)

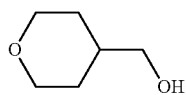 (V)

c) cyclic esters of carbonic acid of general formula VI,

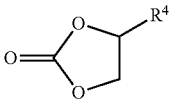 (VI)

wherein $R^4$ is hydrogen, or $C_1$ to $C_2$ hydroxyalkyl; and d) esters of dicarboxyacids of general formula VII

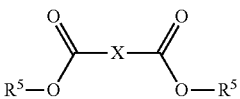 (VII)

wherein X is $C_1$ to $C_6$ alkylene or $C_2$ to $C_6$ alkenylene and $R^5$ is $C_1$ to $C_6$ primary alkyl, or $C_1$ to $C_6$ tertiary alkyl, whereas the composition may optionally further contain auxiliary substances improving the stability and application properties of the solutions, characterized in that it contains 20 to 30% wt/wt of the phosphoric or thiophosphoric triamide derivative of general formula VIII.

* * * * *